United States Patent [19]

Van Heugten

[11] Patent Number: 5,053,014
[45] Date of Patent: Oct. 1, 1991

[54] CATHETER WITH CONTROLLED VALVE

[75] Inventor: Anthony Y. Van Heugten, Tampa, Fla.

[73] Assignee: Critikon, Inc., Tampa, Fla.

[21] Appl. No.: 474,595

[22] Filed: Feb. 1, 1990

[51] Int. Cl.⁵ .............................................. A61M 5/178
[52] U.S. Cl. ..................................... 604/167; 604/198; 604/244; 604/205
[58] Field of Search ................. 604/87, 88, 200–206, 604/164–169, 263, 198, 244

[56] References Cited

U.S. PATENT DOCUMENTS

| | | | |
|---|---|---|---|
| 3,585,996 | 6/1971 | Reynolds et al. | 128/214.4 |
| 4,096,860 | 6/1978 | McLaughlin | 604/167 X |
| 4,177,814 | 12/1979 | Knepshield et al. | 128/348 |
| 4,365,630 | 12/1982 | McFarlane | 604/168 |
| 4,664,654 | 5/1987 | Strauss | 604/198 |
| 4,758,225 | 7/1988 | Cox et al. | 604/126 |
| 4,832,696 | 5/1989 | Luther et al. | 604/164 |
| 4,834,718 | 5/1989 | McDonald | 604/195 |
| 4,842,591 | 6/1989 | Luther | 604/283 |
| 4,850,961 | 7/1989 | Wanderer et al. | 604/53 |
| 4,874,377 | 10/1989 | Newgard et al. | 604/167 |
| 4,917,668 | 4/1990 | Haindl | 604/167 |
| 4,917,669 | 4/1990 | Bonaldo | 604/164 |
| 4,935,010 | 6/1990 | Cox et al. | 604/122 |

Primary Examiner—John D. Yasko
Assistant Examiner—Adam J. Cermak
Attorney, Agent, or Firm—Paul A. Coletti

[57] ABSTRACT

A catheter hub assembly is disclosed wherein the assembly contains a membrane useful in preventing backflow of blood into the flash chamber. The hub assembly contains a membrane opener which operates upon the insertion of a luer locking mechanism into the catheter hub. This membrane opener allows flow of nutritional fluid into the body by causing the opening of the membrane during use of the catheter after removal of the catheter needle.

12 Claims, 3 Drawing Sheets

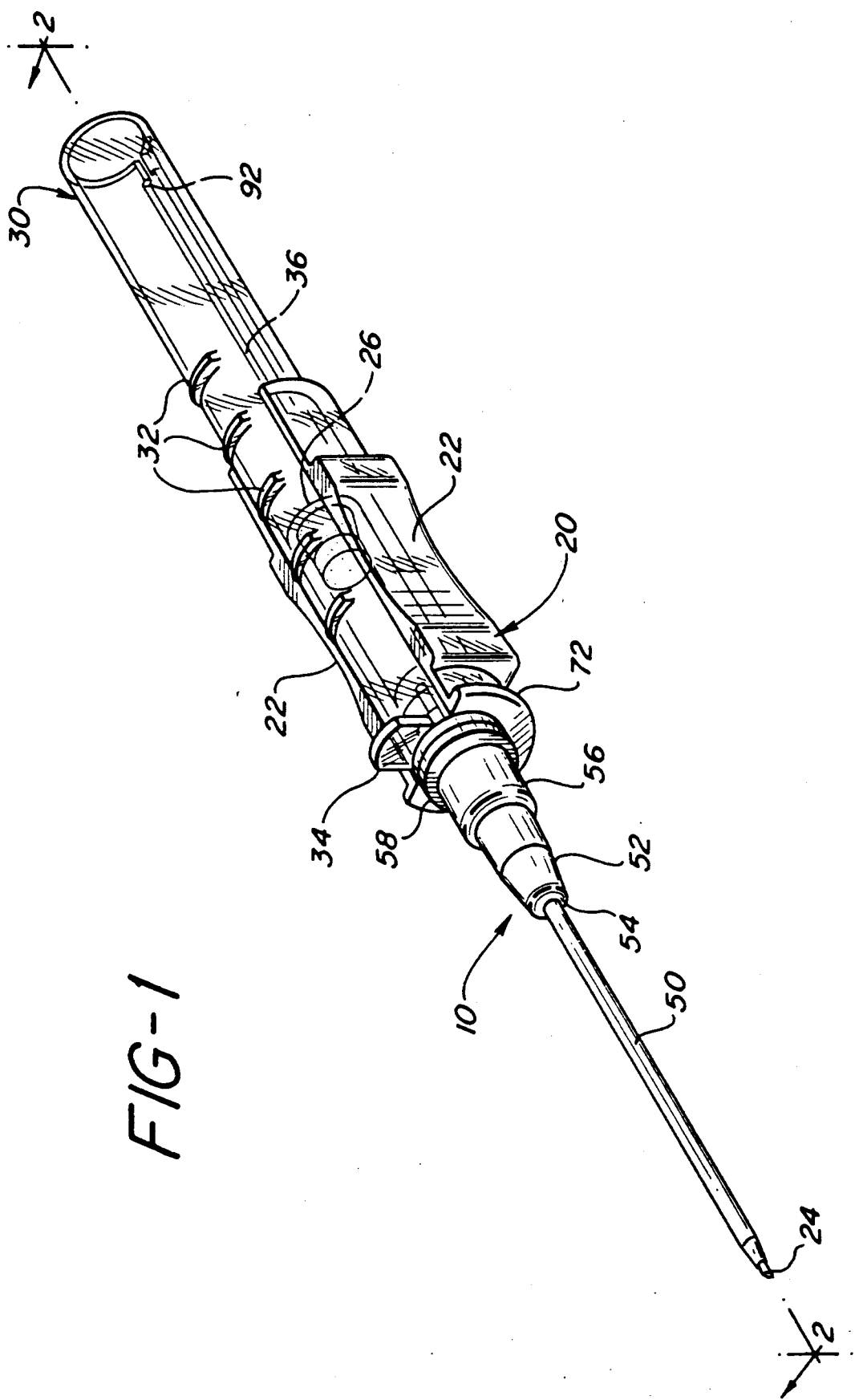

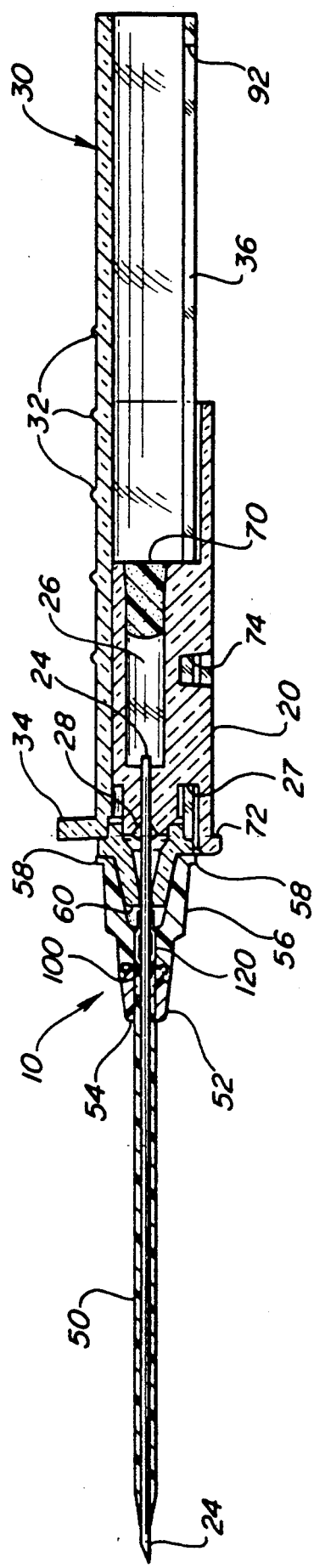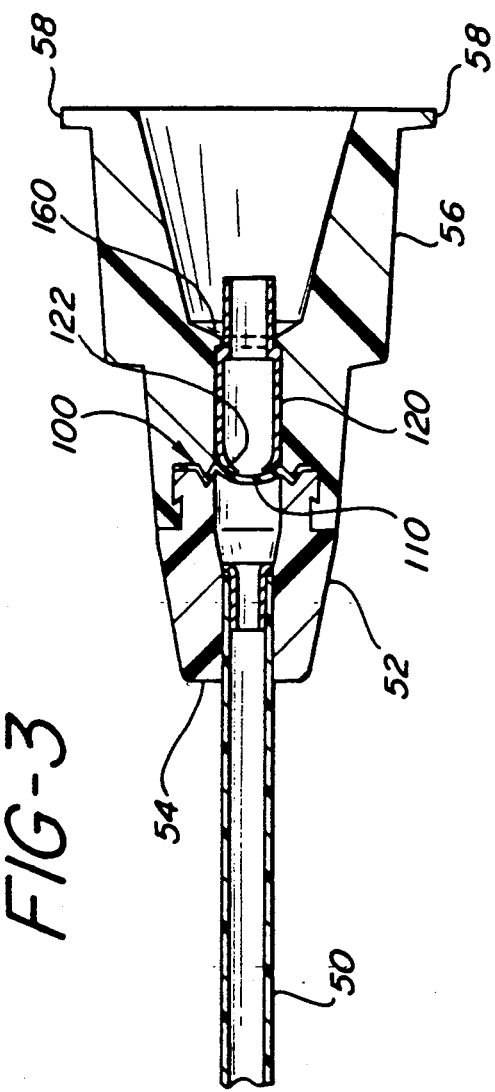

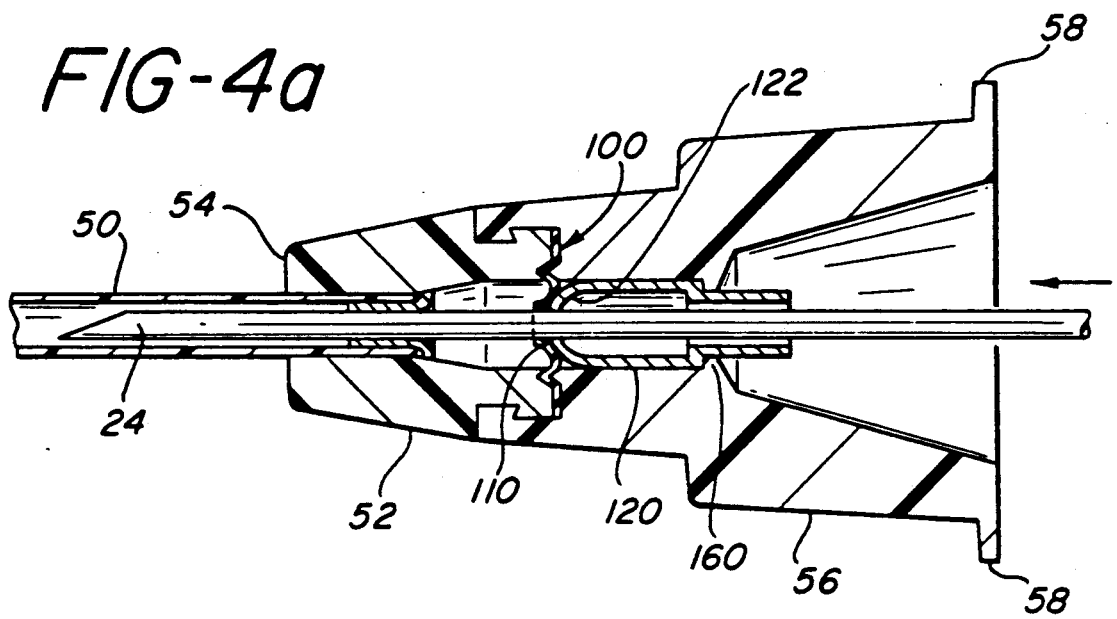
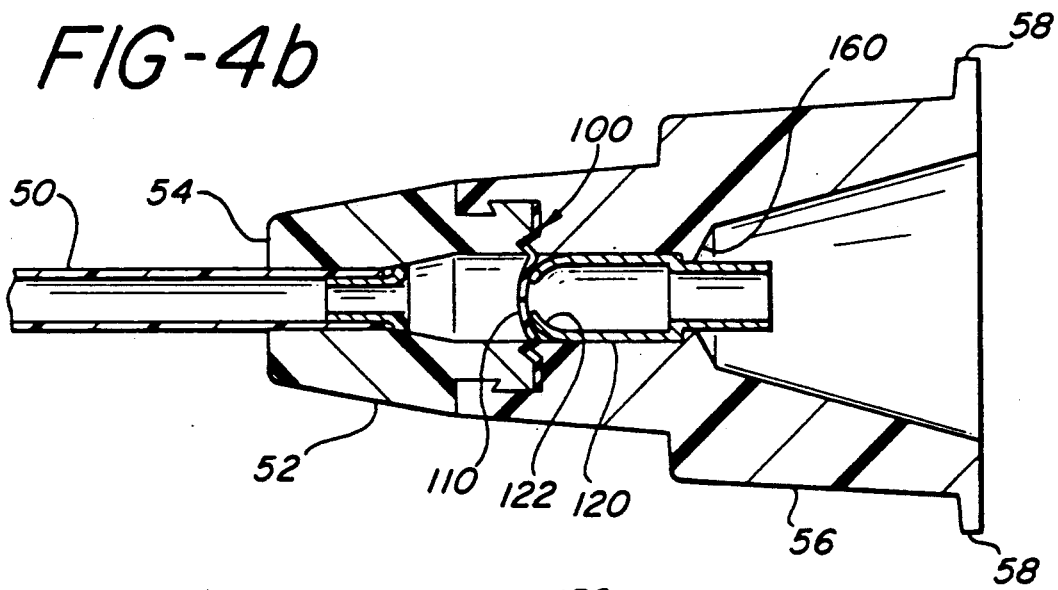
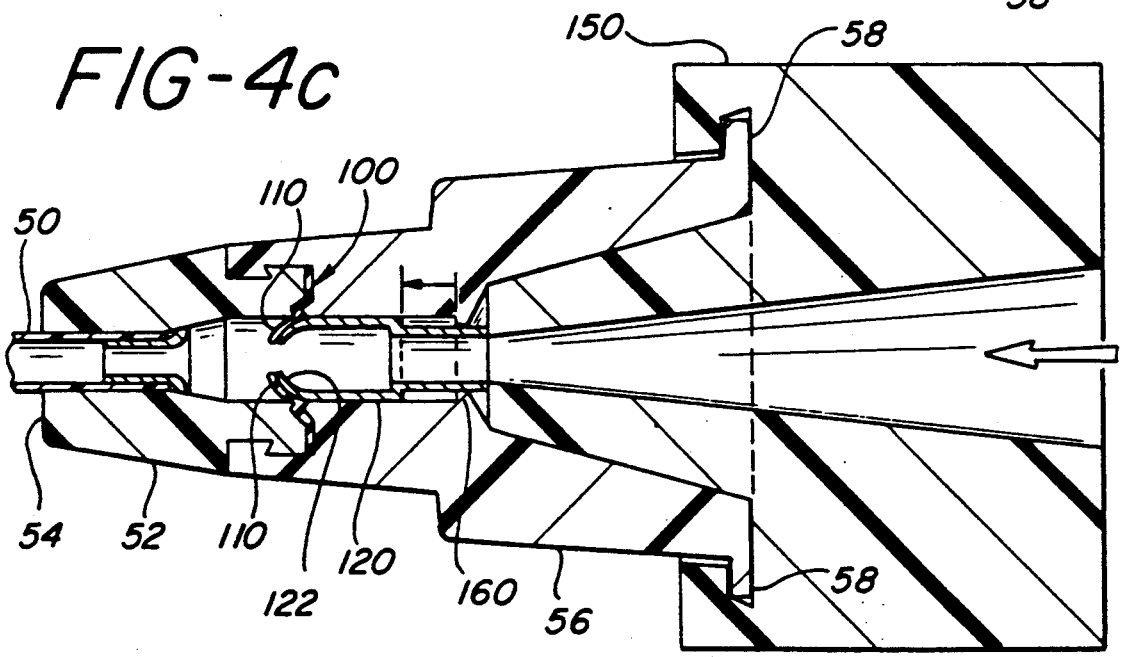

CATHETER WITH CONTROLLED VALVE

This invention relates to I.V. catheters and, in particular, to catheters with valves which open when the catheter is connected to a tubing set.

During use of an I.V. catheter assembly the catheter cannula and its insertion needle are inserted into the body of a patient. When the cannula is properly located in a blood vessel, as evidenced by the appearance of a small amount of blood in the flash chamber of the needle assembly, the needle is withdrawn from the patient and removed from the catheter. A tubing set is then connected to the catheter to deliver fluids to the patient. Throughout this procedure it is desirable to minimize, and preferably eliminate entirely, any blood leakage from the assembly so as to reduce the risk of transmitting blood-borne diseases to medical personnel. In particular, as the needle is withdrawn from the catheter, it would be desirable for a valve mechanism to automatically seal the catheter cannula to prevent blood leakage from the catheter. The cannula should preferably remain sealed until the tubing set is connected to the catheter to for delivery of fluids to the patient. Once the tubing set is connected to the catheter, the assembly is in a fluid-tight condition and subsequent blood leakage is unlikely.

U.S. Pat. No. 3,585,996 describes an arterial catheter placement unit which includes a needle assembly having a needle connected to a needle hub. Located within the needle hub is a self-sealing disc valve made of a relatively thick piece of rubber with several fine slits. The needle hub is designed to connect with a catheter and sheath provided with a sheath hub. Extending from the distal nose of the sheath hub is a hollow pilot tube, through which the catheter is advanced during insertion and threading. When the needle hub is not connected with the sheath hub, the disc valve is in its normally closed condition, preventing blood leakage from the hub. When the sheath hub is connected to the needle hub, the pilot tube on the sheath hub nose extends through the valve disc to hold the valve open and allow the catheter to be threaded through the valve. After the sheath hub is removed from the needle hub, the valve automatically closes and prevents flow of blood from the artery through the needle.

It would be desirable to apply the valve principle of the '996 patent to a catheter assembly to enable the catheter to automatically open when an insertion needle is passed through the catheter, then automatically close when the needle is withdrawn from the catheter, then automatically open when a tubing set is connected to the catheter. The assembly must thus be capable of these specific modes of operation with the various ancillary components listed in order to prevent blood leakage from the catheter prior to connection of the catheter to a tubing set.

In accordance with the principles of the present invention, a catheter assembly is provided, including a catheter cannula connected to a catheter hub. Located within the catheter hub is a normally closed valve membrane. The valve membrane is opposed by a moveable valve membrane opener. When the catheter and hub are connected to an insertion needle assembly the insertion needle passes through the membrane opener and the valve membrane. When the needle is withdrawn from the membrane opener and membrane the membrane automatically seals the passageway of the catheter hub. When a tubing set is connected to the catheter hub, the tubing set connector actuates the valve membrane opener to open the valve membrane so that fluids may be delivered through the catheter to a patient.

In the drawings:

FIG. 1 is a perspective view of a catheter assembly constructed in accordance with the principles of the present invention;

FIG. 2 is a cross-sectional view of the catheter assembly 2—2 of FIG. 1;

FIG. 3 is a detailed cross-sectional view of the catheter and catheter hub of the assembly of FIGS. 1 and 2; and FIGS. 4a–4c illustrate a catheter and catheter hub of the present invention during various stages of use.

Referring first to FIG. 1, a catheter assembly constructed in accordance with the principles of the present invention is shown in perspective.

Referring first to FIG. 1, a catheter assembly 10 constructed in accordance with the principles of the present invention is shown. The assembly 10 includes a needle housing 20 which is semi-tubular in shape and open at the top. Molded on the sides of the needle housing 20 are opposing contoured finger grips 22, one of which is visible in FIG. 1. Located inside the semi-tubular needle housing and extending proximally therefrom is a tubular needle guard 30. On the upper surface of the needle guard are a number of small projections 32 which provide surfaces against which a user may press to fully extend the needle guard. These projections permit a user to extend the needle guard with the index or other finger while holding the catheter assembly with one hand. Extending distally from the needle housing 20 is a protective sheath not shown which covers the distally extending needle and catheter.

FIG. 2 illustrates the assembly of FIG. 1 after removal of the protective sheath. This drawing shows the catheter 50 and its catheter hub 52 mounted on the distal end of the needle guard 30. The point of the needle 24 is seen to extend from the distal tip of the catheter 50. A push-off tab 34 is seen projecting upward from the needle guard proximal the catheter hub 52. Located on the distal end of the needle guard is a needle guard tip 60, through which the needle 24 extends.

FIG. 2 also serves as a cross-sectional view of the catheter assembly 10. The catheter 50 is seen to extend from the distal end 54 of the catheter hub 52 and is concentric therewith. The catheter may be attached to its hub by any means known in the art, including adhesively or mechanically by means of a metal eyelet. The larger diameter proximal portion 56 of the catheter hub 52 is flanged at its proximal end for connection to an infusion set, and the inner diameter of the proximal portion of the hub is sized to fit over the distal portion of the needle guard tip 60.

The needle 24 is attached to the distal end of the flash chamber 26 of the needle housing with the proximal end of the needle 24 terminating within the chamber. The needle 24 is affixed in place by adhesive 28. The needle extends through the needle guard tip 60, the catheter hub 52, and the catheter 50, with the point of the needle extending from the distal end of the catheter. The rear of the flash chamber 26 is plugged by a microporous plug 70. The needle guard is seen to extend proximal the rear of the needle housing with the needle guard tip 60 affixed to the distal end of the needle guard at the location of the push-off tab 34. The tubular needle guard surrounds the flash chamber 26, with the base 27 of the flash chamber being located in a longitudinal slot 36 at the bottom of the needle guard. As the needle guard slides in the distal direction to cover the needle it is maintained concentric with the needle housing by the concentric tubular construction of the needle housing and needle guard and by the tracking of the base 27 of the flash chamber in the needle guard slot 36.

A flange 72 is formed at the distal end of the housing. The flash chamber 26 is seen to be centrally located in the housing. Needle guard 30 and housing 20 slide together until the narrowed proximal end 92 of needle guard slot 36 engages the aperture 74 of the housing, causing the two components to lock together. An instrument is inserted into the aperture 74 and into slot 36 to spread the narrowed portion 92 of the slot and thereby permit the needle guard to proceed fully into the needle housing.

The concentric tubular construction of the needle guard and housing also permits the needle guard to slide into the housing from the proximal end of the housing. Thus, the catheter device can then be assembled without causing the needle guard 30 to pass through its locking position, thereby obviating the need to unlock the narrowed portion 92 of the guard slot during assembly of the device.

The catheter assembly of FIG. 2 may be used in the conventional manner by inserting the concentric catheter and needle through the skin of a patient and into a blood vessel. When the point of the needle 24 is properly located in the vessel, a small amount of blood will flow through the needle and into the flash chamber 26. Since the needle housing and guard are made of transparent or translucent polymeric materials, the flow of blood will be readily apparent in the flash chamber. The needle is then retracted from the vessel and the catheter 50 threaded into the vessel by grasping the finger grips 22 of the housing with the thumb and fingers and pushing the push-off tab 34 in the distal direction with one finger. This motion will push the catheter hub 52 off of the needle guard tip 60 to advance the catheter. As the needle guard begins to extend out from the distal end of the needle housing such that the push-off tab 34 is beyond the reach of the finger of the user, the user may engage the projections 32 with the finger to continue the distal motion of the needle guard.

Finally this motion will result in proper threading of the catheter into the vessel and the complete withdrawal of the needle from the patient's body. The needle guard 30 is then advanced to its fullest extension. As it does so, the tapered proximal section of the flash chamber 26 will spread the narrowed proximal portion 92 of the needle guard slot 36 until the narrowed portion 92 engages aperture 74. At the fullest extension of the needle guard from the housing the engagement of the narrowed portion 92 in the aperture 74 will lock the needle guard 30. The needle 24, housing 20 and guard 30 may then be set aside without concern for inadvertent injury to the user or others.

As better seen in FIGS. 3, 4a, 4b and 4c, there is shown the catheter 50 and catheter hub 52 assembly incorporated with the membrane assembly 100 of the invention. This membrane assembly 100 is spaced within catheter hub 52 and comprises a one-directional valve membrane 110. This valve membrane is originally sealed before the needle 24 is inserted into the catheter 50. This valve membrane 110 comprises essentially a malleable gasket material, such as known plastics, rubber, or any other one-directional valve material. Upon insertion of the plastic hub introducer needle 24 into the catheter 50 assembly, the membrane 110 is punctured, as is better seen in FIG. 4a. Accordingly, the remainder of the introduction of needle 24 into the patient remains according to currently preferred procedures.

As is better seen in FIG. 4b, the needle 24 is removed from the catheter 50 and catheter hub 52 assembly. Upon removal from the catheter hub 52, the valve membrane 110 closes. It is to be noted that upon removal of the needle 24 two significant improvements to operation of the catheter assembly 10 are realized. First, unlike in other systems, the present catheter assembly 10 prevents leakage of blood through catheter 50 into flash chamber 26. Normally, blood flowing out of the body has an approximate pressure of about 2 psi. The valve membrane 110 is configured so that it withstands outwardly directional flow of blood greater than about 3 psi or well above the normal human limit, through catheter 50 into flash chamber 26. Also, even though valve membrane 110 is inserted into the catheter assembly 10, the valve membrane 110 is configured so that there is no frictional drag on needle 24 during its retraction from the catheter 50. This is so because valve membrane 110 is generally configured as a "duck-bill" valve or a valve of similar configuration and smoothly allows removal of the needle 24 from the catheter. Upon removal of the needle 24 from the catheter 50, the valve membrane unidirectionally closes so that blood will not flow into flash chamber 26.

As is further seen in FIGS. 3 and 4c, hub 52 also contains membrane opener 120. Membrane opener 120 is generally cylindrical in shape and contains nose-shaped opening means 122. These nose shaped opening means 122 fit comfortably within valve membrane 110 when so inserted. Also attached to catheter hub 52 is collar mechanism 160. This collar mechanism 160 holds membrane opener 120 in place when luer assembly 150 is attached to catheter hub 52. Upon attachment of luer assembly 150 to catheter hub 52 at flanges 58, intravenous fluids are connected with the catheter 50 so that they may be diffused into the body.

As luer assembly 150 is being attached to catheter hub 52, collar mechanism 160 holds membrane opener 120 in place so that nose-shaped opening means 122 of membrane opener 120 proceed to open valve membrane 110. This is best seen in FIG. 4c. Thus, when the valve membrane 110 is open, nutritional fluids are able to be disposed into the body.

Importantly, even though luer assembly 150 now forces open membrane opener 120, there is no significant increase in the force necessary to attach luer assembly 150 to catheter hub 52, or to open valve membrane 110. Accordingly, practicing the catheter control valve assembly of this invention causes no additional steps or exertion by the user. In addition, opening means 122 is created so that it opens valve membrane 110 as wide as is necessary to maintain flow rates within catheter 50. Accordingly, the same flow rates within catheter 50 are realized. In this way, performance is not compromised during practice of this invention.

Thus, a valved catheter hub assembly is disclosed as above described. It is to be realized that the invention described by this control valve assembly is to be seen in the following claims and equivalents.

What is claimed is:
1. A catheter assembly comprising:
a semi-tubular needle housing having an open top;

a flash chamber located in the interior of said needle housing and having a hollow needle extending from the distal end thereof;

a tubular needle guard having a proximal end and a distal end, slideably located within said needle housing and including an aperture at its distal end for passage of said hollow needle therethrough and containing said flash chamber;

a catheter and catheter hub assembly suitable for mounting on the distal end of said needle guard; and a valve and valve opener assembly held within said hub wherein said opener is slideably emplaced in said hub such that said opener is not engageable with said needleguard, and wherein said hub is attachable to a luer assembly such that with said luer assembly attached to said hub, said valve opener contacts said luer assembly and slides to open said valve.

2. In the assembly of claim 1, said valve for permitting flow of fluid from said opener side to said catheter side, and rejecting flow from said catheter side to said opener side when said valve opener is not engaged with said valve.

3. In the assembly of claim 2, said valve halting flow to about 3 psi.

4. In the assembly of claim 2, said valve comprising a duck-bill valve.

5. In the assembly of claim 4, said needle retractable out of said valve while maintaining a seal from fluid flow from said catheter side to said opener side.

6. A catheter assembly comprising:

a semi-tubular needle housing having an open top;

a flash chamber located in the interior of said needle housing and having a hollow needle extending from the distal end thereof;

a tubular needle guard having a proximal end and a distal end, slideably located within said housing and including an aperture at its distal end for passage of said hollow needle therethrough and containing said flash chamber;

a catheter and catheter hub assembly suitable for mounting on the distal end of said needle guard; and a valve and valve opener assembly emplaced in said hub such that said opener is not engageable with said needle guard.

7. In the assembly of claim 6, said valve permitting flow of fluid from said opener side to said catheter side, and rejecting fluid flow from said catheter side to said opener side, when said nose-shaped end is not engaged with said membrane.

8. The assembly of claim 6 wherein said hub is attachable to the luer assembly such that with said luer assembly attached to said hub, said valve opener contacts said luer assembly and slides to open said valve.

9. In the assembly of claim 6, said valve sealed to fluid flow from said catheter side to said flash chamber side.

10. In the assembly of claim 6, said membrane halting flow to about 3 psi.

11. In the assembly of claim 6, said membrane comprising a duck-bill valve.

12. In the assembly of claim 6, said opener having a nose-shaped end insertable within said membrane to open said membrane and allow fluid flow across said valve.

* * * * *